United States Patent [19]

Wu

[11] Patent Number: 5,448,788
[45] Date of Patent: Sep. 12, 1995

[54] THERMOELECTRIC COOLING-HEATING MATTRESS

[76] Inventor: Shuenn-Jenq Wu, 7F, No. 10, Sec. 2, Ming-Sheng East Rd., Taipei, Taiwan

[21] Appl. No.: 207,218

[22] Filed: Mar. 8, 1994

[51] Int. Cl.⁶ ............................................. A61F 7/03
[52] U.S. Cl. ......................................... 5/421; 5/462; 62/261
[58] Field of Search ........................... 5/421, 423, 462; 62/261

[56] References Cited

U.S. PATENT DOCUMENTS

| | | | |
|---|---|---|---|
| 800,967 | 10/1905 | Young et al. | 5/421 X |
| 2,938,356 | 5/1960 | McMahon | 62/261 X |
| 3,283,520 | 11/1966 | Donohue et al. | 62/261 X |
| 3,648,469 | 3/1972 | Chapman | 5/421 X |
| 4,907,308 | 3/1990 | Leininger et al. | 5/462 X |
| 5,146,633 | 9/1992 | Kim et al. | 5/421 |

Primary Examiner—Michael F. Trettel
Attorney, Agent, or Firm—Beveridge, DeGrandi, Weilacher & Young

[57] ABSTRACT

A thermostat controlled mattress includes a mattress unit having an underlay, a surface cover and a curved circuit. A water circuit tube connects to the curved circuit so as to allow water to be introduced into the mattress unit with the aid of a pump. Water is circulated between the mattress unit and a water storage box via the water circuit tube. A sensor is operatively arranged with respect to the water storage box to sense the temperature and quantity of water contained in the water storage box and sends a signal to a thermostat electric circuit. An aluminum reservoir for the water is connected to the curved circuit of the mattress unit and the water circuit tube. A thermoelectric element is connected to the reservoir and the power supply to heat or cool the water. Water is circulated in the water circuit tube between the curved circuit of the mattress unit and the water storage box, through the reservoir. The water temperature is controlled based on signals generated by the thermostat electric circuit, which activates the power supply operatively connected to the thermoelectric element. A heat sink and a fan may be arranged adjacent to the thermoelectric element such that the fan blows a current of air onto the heat sink.

17 Claims, 2 Drawing Sheets

THERMOELECTRIC COOLING-HEATING MATTRESS

BACKGROUND OF THE INVENTION

In conventional mattress designs, one method of adjusting and controlling temperature is to pour hot water or ice filling into the mattress to change its surface temperature, to thereby attain a comfortable temperature. Another known method of controlling the temperature includes setting up an electric heating resistor within the mattress to raise the temperature of the mattress for use in winter. However, the foregoing process of pouring hot water or ice filling into the mattress requires effort to maintain the temperature, and additional effort to adjust the temperature to the user's setting. Adopting the process using the electric resistor also has its shortcomings. Upper temperature readings are difficult to achieve, and it is difficult to radiate heat. The above processes make it inconvenient to use the mattress and require further improvement.

SUMMARY OF THE INVENTION

The present invention is a thermoelectric transistor thermostat mattress, consisting of a thermoelectric transistor, a water storage box, a motor pump, a fan, a heat sink, an aluminum reservoir, and a liquid circuit. These devices are employed in producing a liquid thermoelectric exchange current by means of a thermostat electric circuit which controls the fan and a thermoelectric cooler transistor. A sensor is used to transfer information regarding water temperature and quantity from the water storage box to the thermostat electric circuit. In response to this information, the power supply is adjusted according to the status of the indicator. Powered by the motor pump's thermoelectric exchange current, heat is transferred to adjust the mattress temperature, either upward or downward, to the desired value. Accordingly, the mattress in accordance with the invention improves the sleep and the quality of leisure. Consequently, the improved temperature control increases productivity.

DETAILED DESCRIPTION OF THE PREFERRED EMBODIMENT

Figure 1:
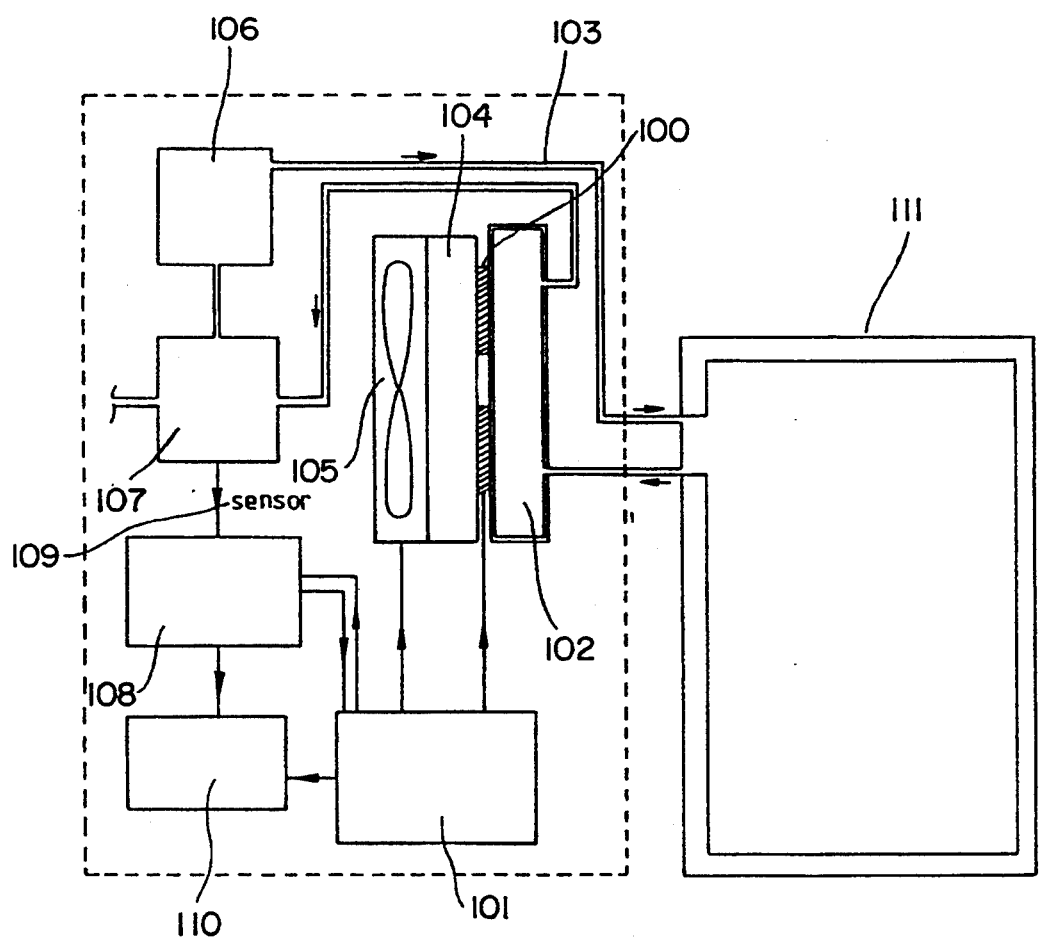
FIG. 1 is an overview of the invention's structure and process.

FIG. 1 shows the invention's structure and process. By supplying power in different directions from a power supply 101 to a thermoelectric cooler (or thermoelectric element) 100, which power supply 101 receives information from a thermostat electric circuit 108, the thermoelectric cooler 100 is heated or cooled. One side of the thermoelectric cooler 100 connects with an aluminum reservoir 102. Besides producing thermostat efficacy, the thermoelectric cooler 100 causes a change in temperature in the water current in the circuit 103 through the aluminum reservoir 102 which is connected to the circuit 103, as shown in FIG. 1. The other side of the thermoelectric cooler 100 connects with the heat sink 104. A current of air is blown by fan 105 into the heat sink 104, producing a radiating function. The fan 105 is operated by the power supply 101. The water circulation in tube or circuit 103 is powered by a pump 106, forming a current. The water concentrates in the water storage box 107, where a sensor 109 measures its temperature and quantity. The sensor 109 controls the power supply 101, appropriately switching the fan 105, reversing the power of the transistor of the thermoelectric cooler 100 on and off, in accordance with the information received. The power supply 101 and thermostat electric circuit 108 transfer conditioned signals to the indicator 110. The user can see and recognize the entire procedure of thermostat installation. The two ends of the circuit 103 form a closed feedback loop beginning and ending with a single mattress 111. Accordingly, by means of the thermoelectric function of the transistor of the thermoelectric cooler 100, the mattress 111 is maintained at an ideal temperature.

Figure 2:
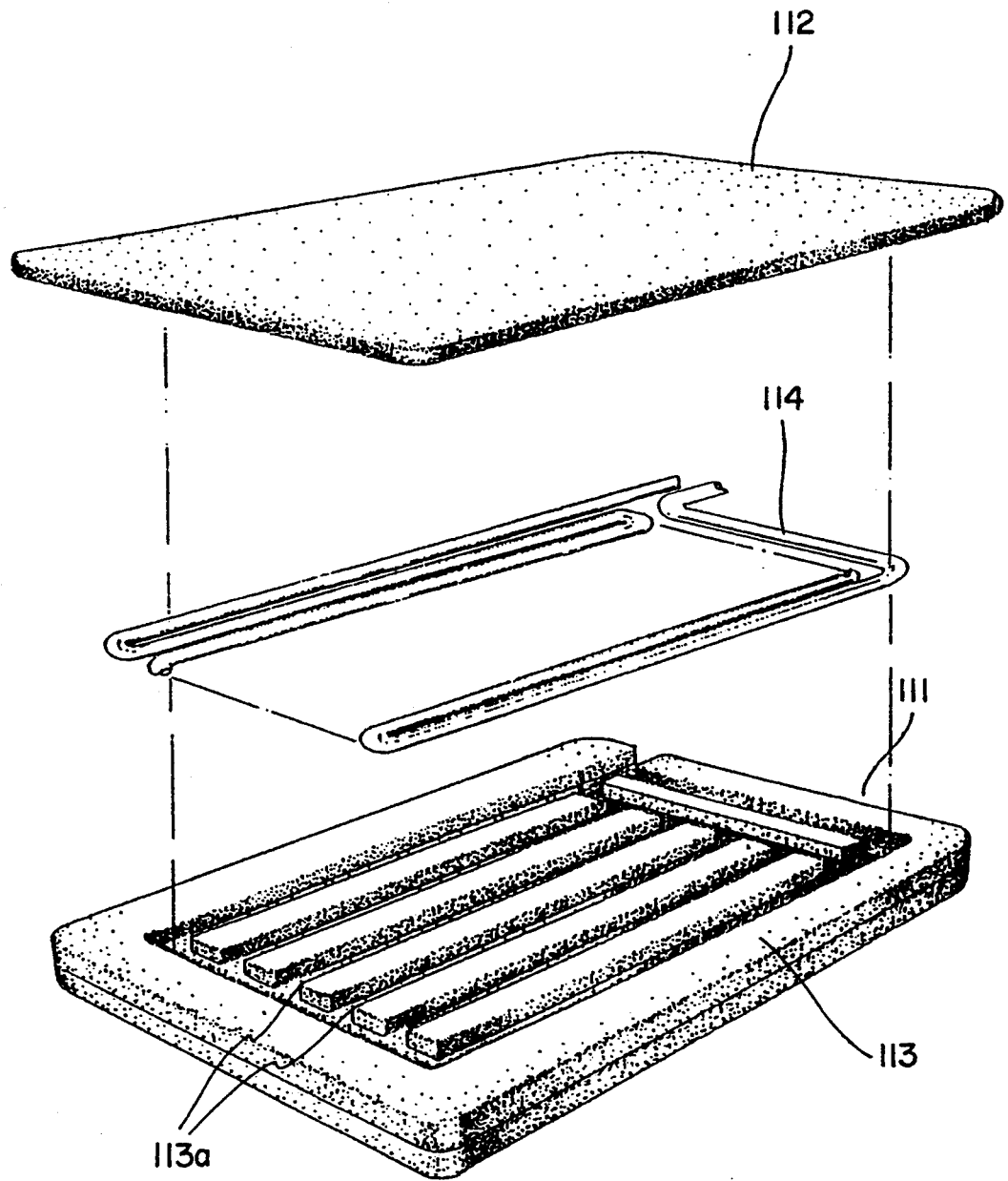
FIG. 2 is an exploded view showing some of the features of one embodiment of the mattress in accordance with the invention.

FIG. 2 illustrates the features of an embodiment of the mattress 111 in accordance with the invention. As shown in the drawing, a curved circuit 114 is placed between the mattress surface 112 and the underlay 113. Part of the underlay 113 forms a concave channel 113a, allowing the installation of the curved circuit 114. The thermoelectric cooler 100 is used to cause the surface of the mattress 111 to achieve an ideal temperature. Therefore, no matter how hot it gets in the summer, or how cold it gets in the winter, this invention—the improved mattress—can be satisfactorily controlled to provide an ideal temperature, the key area of improvement provided by this invention.

What is claimed is:

1. A thermostat controlled mattress, comprising:
   a mattress unit;
   a water circuit tube connected to the mattress unit so as to allow water to be introduced into the mattress unit;
   a water storage box connected to the water circuit tube to hold water;
   a sensor operatively arranged with respect to the water storage box to sense the temperature and quantity of water contained in the water storage box;
   a thermostat electric circuit responsive to the sensor;
   a power supply operatively connected to the thermostat electric circuit;
   a reservoir connected to the mattress unit and the water circuit tube; and
   a thermoelectric element operatively connected to the reservoir and the power supply;
   whereby water is circulated in the water circuit tube between the mattress unit and the water storage box, through the reservoir, and whereby the water temperature is controlled based on signals generated by the thermostat electric circuit, which activates the power supply operatively connected to the thermoelectric element.

2. A thermostat controlled mattress of claim 1, further including a pump to circulate the water in the water circuit tube between the water storage box and the mattress unit.

3. A thermostat controlled mattress of claim 1, further including a heat sink connected to the thermoelectric element.

4. A thermostat controlled mattress of claim 3, further including a fan arranged adjacent to the heat sink such that the fan blows a current of air onto the heat sink to thereby form a radiator.

5. A thermostat controlled mattress of claim 1, wherein the thermoelectric element includes a transistor.

6. A thermostat controlled mattress of claim 1, further including an indicator connected to the thermostat electric circuit and the power supply.

7. A thermostat controlled mattress of claim 1, wherein the mattress unit includes an underlay and a surface cover.

8. A thermostat controlled mattress of claim 7, wherein the mattress unit includes a curved circuit which connects to the water circuit tube.

9. A thermostat controlled mattress of claim 8, wherein the underlay of the mattress unit has a concave channel defined therein, wherein the curved circuit is arranged in the concave channel.

10. A thermostat controlled mattress of claim 1, wherein the mattress unit includes a curved circuit which connects to the water circuit tube.

11. A thermostat controlled mattress of claim 10, wherein the mattress unit has a concave channel defined therein, wherein the curved circuit is arranged in the concave channel.

12. A thermostat controlled mattress of claim 1, wherein the reservoir is made from aluminum.

13. A thermostat controlled mattress, comprising:
a mattress unit including an underlay, a surface cover and a curved circuit;
a water circuit tube connected to the curved circuit of the mattress unit so as to allow water to be introduced into the mattress unit;
a water storage box connected to the water circuit tube to hold water;
a sensor operatively arranged with respect to the water storage box to sense the temperature and quantity of water contained in the water storage box;
a thermostat electric circuit responsive to the sensor;
a power supply operatively connected to the thermostat electric circuit;
a reservoir connected to the curved circuit of the mattress unit and the water circuit tube;
a pump to circulate the water in the water circuit tube between the water storage box and the curved circuit of the mattress unit;
a thermoelectric element operatively connected to the reservoir and the power supply;
an indicator connected to the thermostat electric circuit and the power supply;
whereby water is circulated in the water circuit tube between the curved circuit of the mattress unit and the water storage box, through the reservoir, and whereby the water temperature is controlled based on signals generated by the thermostat electric circuit, which activates the power supply operatively connected to the thermoelectric element.

14. A thermostat controlled mattress of claim 13, further including a heat sink connected to the thermoelectric element.

15. A thermostat controlled mattress of claim 14, further including a fan arranged adjacent the heat sink such that the fan blows a current of air onto the heat sink to thereby form a radiator.

16. A thermostat controlled mattress of claim 13, wherein the underlay of the mattress unit includes a concave channel defined therein, wherein the curved circuit is arranged in the concave channel.

17. A thermostat controlled mattress of claim 13, wherein the reservoir is made from aluminum.

* * * * *